United States Patent [19]
Preikschat et al.

[11] Patent Number: 5,619,043
[45] Date of Patent: Apr. 8, 1997

[54] SYSTEM FOR ACQUIRING AN IMAGE OF A MULTI-PHASE FLUID BY MEASURING BACKSCATTERED LIGHT

[75] Inventors: Ekhard Preikschat, Bellevue; Jon V. Hokanson, Redmond; Barry W. Reed, Auburn, all of Wash.

[73] Assignee: Laser Sensor Technology, Inc., Redmond, Wash.

[21] Appl. No.: 310,630

[22] Filed: Sep. 21, 1994

[51] Int. Cl.$^6$ .................................................. G01N 21/49
[52] U.S. Cl. .................... 250/574; 250/216; 250/564; 356/342; 356/336
[58] Field of Search .............................. 250/208.1, 573, 250/574, 222.2, 564, 216, 227.23, 227.24; 356/335, 336, 342, 343

[56] References Cited

U.S. PATENT DOCUMENTS

| | | | |
|---|---|---|---|
| 4,179,218 | 12/1979 | Erdmann et al. | 356/336 |
| 4,245,909 | 1/1981 | Loos | 356/336 |
| 4,492,467 | 1/1985 | Drain et al. | 356/336 |
| 4,529,306 | 7/1985 | Kilham et al. | 356/237 |
| 4,871,251 | 10/1989 | Preikschat et al. | 356/336 |
| 5,191,388 | 3/1993 | Kilham | 356/335 |
| 5,377,005 | 12/1994 | Meyer | 356/335 |
| 5,383,024 | 1/1995 | Maxey et al. | 356/336 |

*Primary Examiner*—Edward P. Westin
*Assistant Examiner*—Stephen Calogero
*Attorney, Agent, or Firm*—Christensen, O'Connor, Johnson & Kindness

[57] ABSTRACT

The present invention describes an optical technique for analyzing undiluted, multi-phase fluid flows as typically encountered inside reactor vessels or flow lines in the chemical industries. In particular the technique uses a pulsed, coherent light source and measures the back-scattered light collected over a wide scattering angle. A light beam is relayed via a set of lenses down a long probe tube, through a window at a probe tip to illuminate the material that is passing past the window. The light beam is pulsed to "freeze" the motion of the particles streaming past the window. The backscattered light is collected by the same set of optics and is focused on the front surface of a CCD chip. The lens closest to the front window has a short focal length with a large numerical aperture to collect the back-scattered light over a wide range of backward angles, thereby increasing the detection sensitivity to larger particles, which lie behind and are partially obscured by the myriad of smaller particles closest to the window. The probe tube is inserted through an insertion assembly so that the front viewing window is in direct contact with the material flow, and can be positioned so that the flow will provide a continuous and representative stream of material past the window. Best measuring conditions are obtained by placing the probe window at a modest angle of 30°–45° into the flow. The preferred embodiment combines imaging technology with a specific probe configuration, which is optimized for use in the chemical process industries.

2 Claims, 9 Drawing Sheets

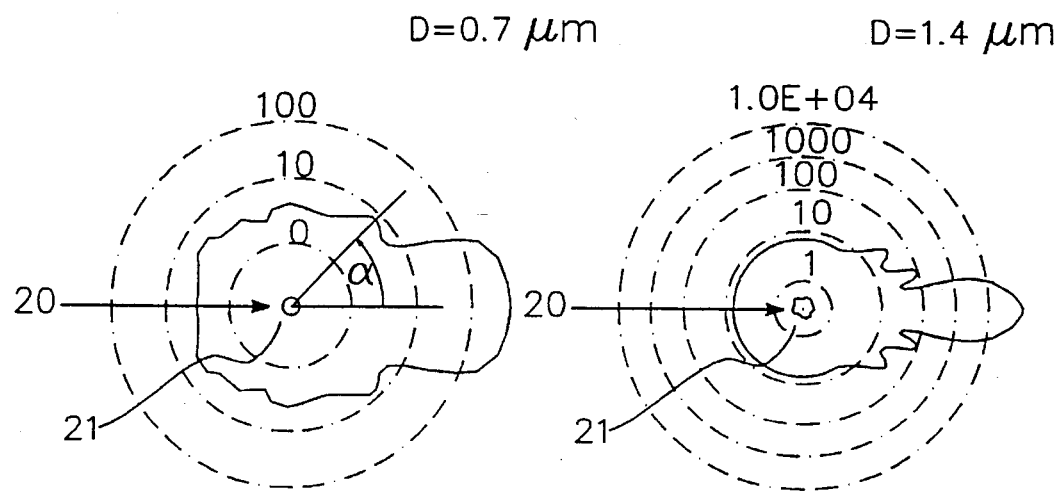
D=0.7 μm   D=1.4 μm
*Fig. 3A.*   *Fig. 3B.*
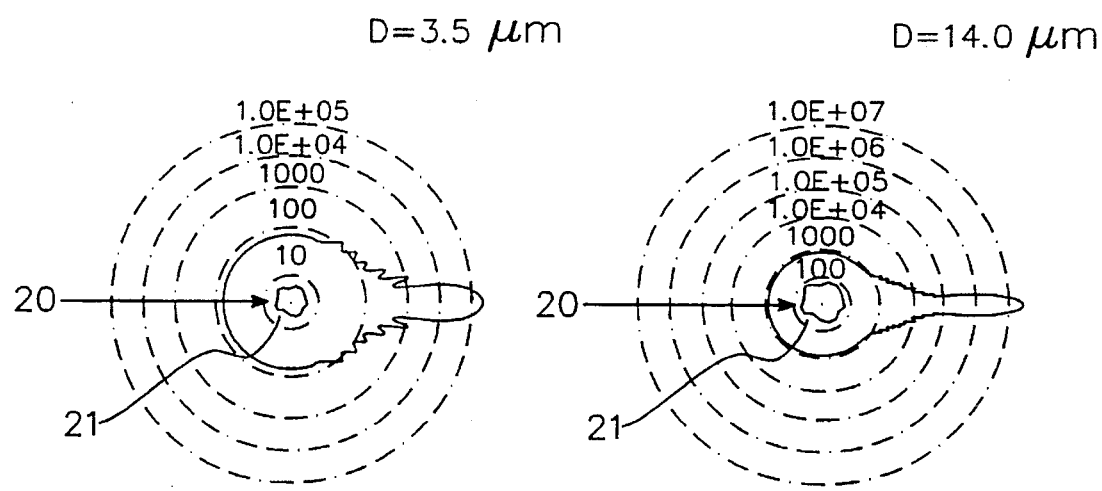
D=3.5 μm   D=14.0 μm
*Fig. 3C.*   *Fig. 3D.*

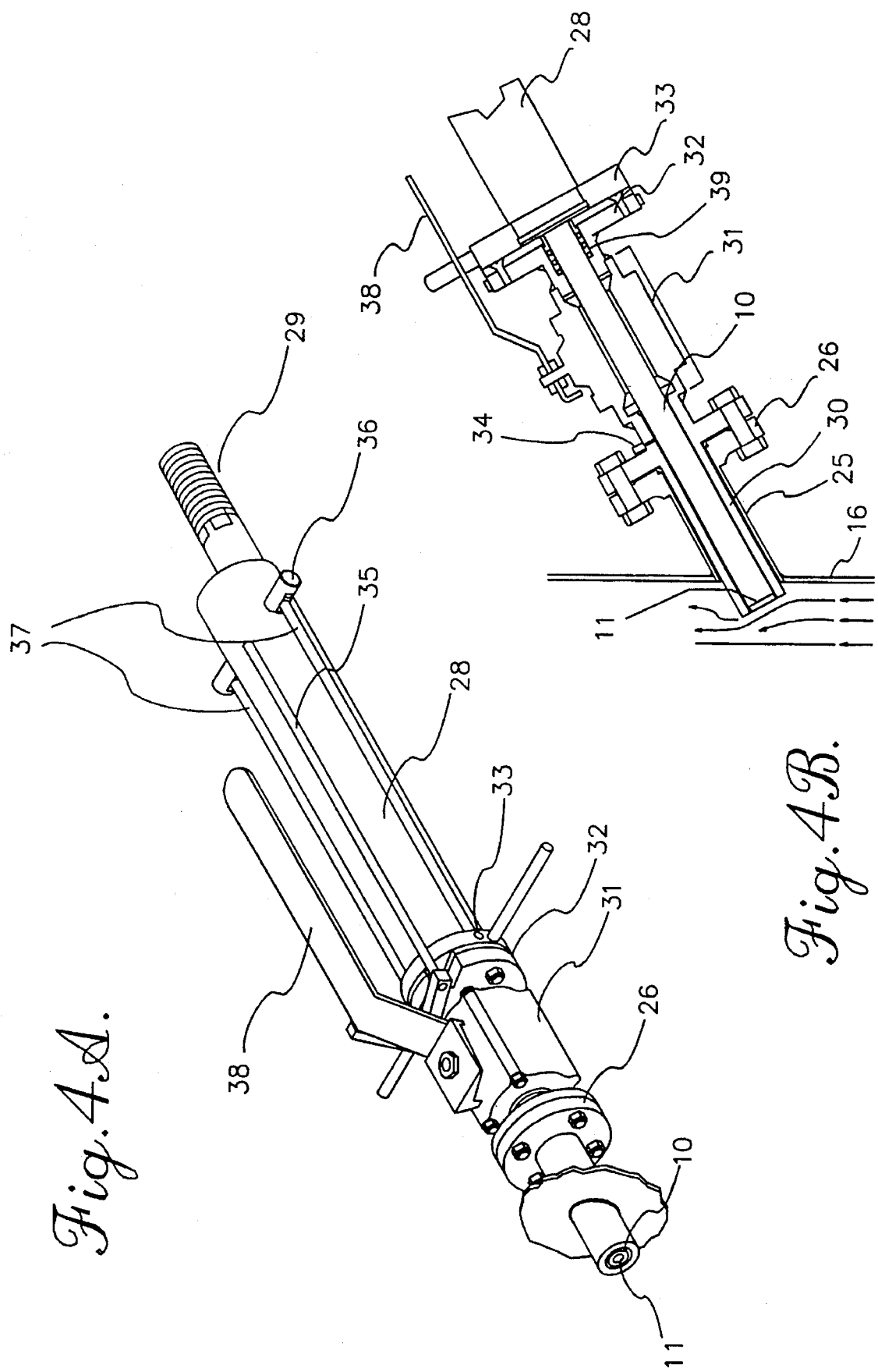

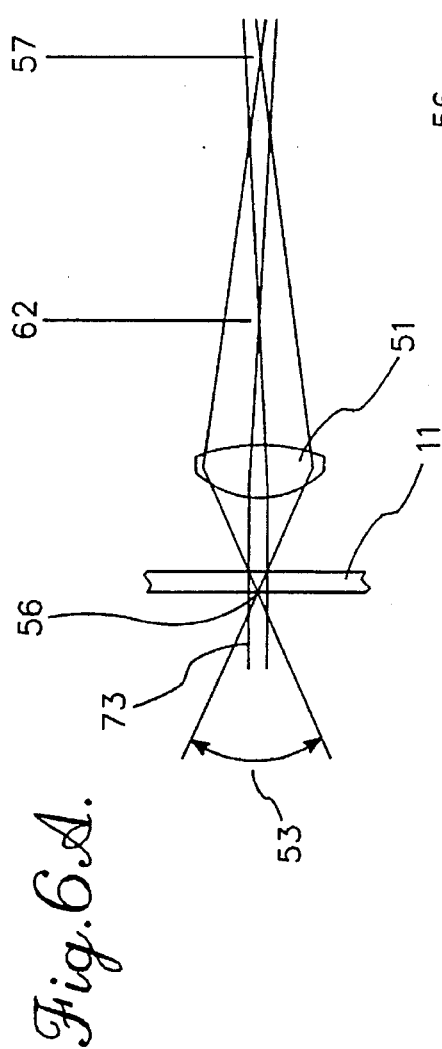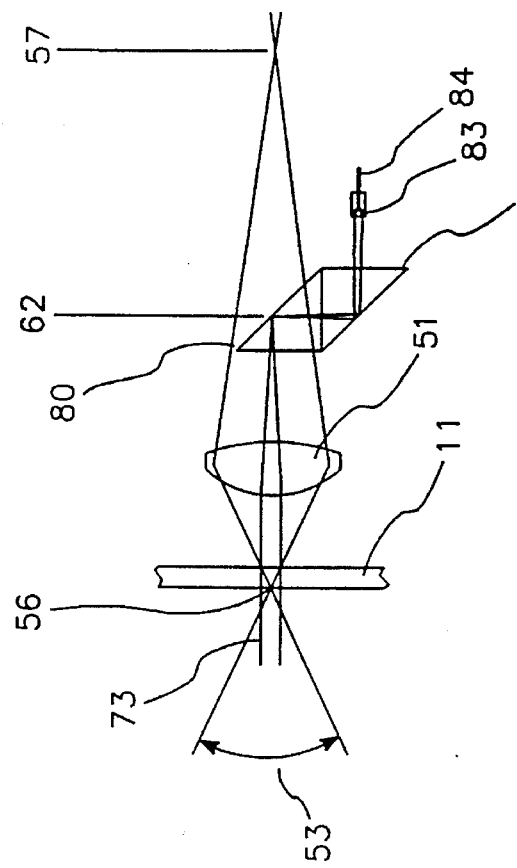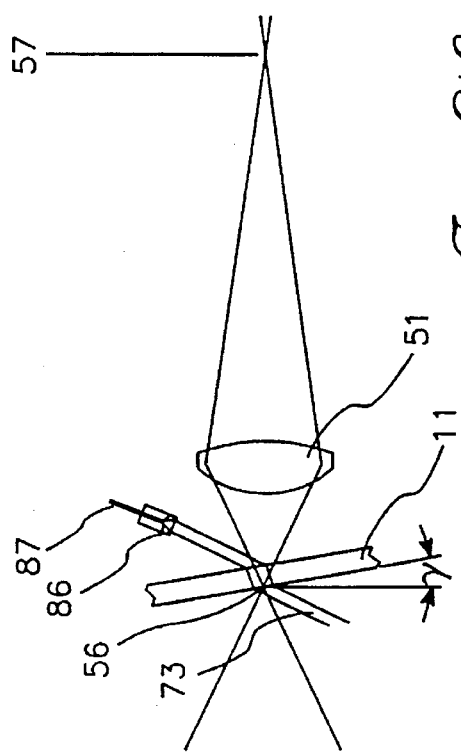

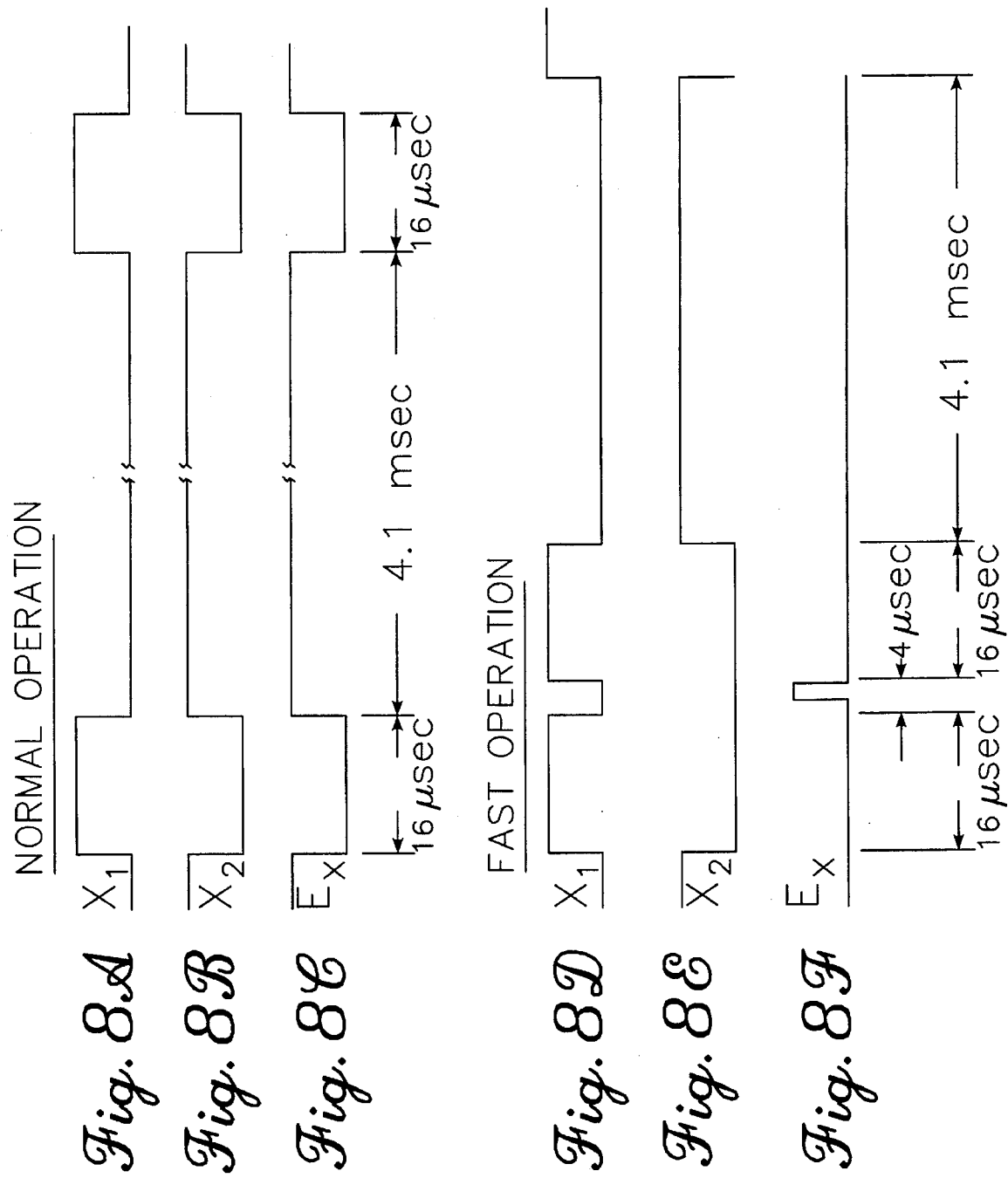

NORMAL OPERATION
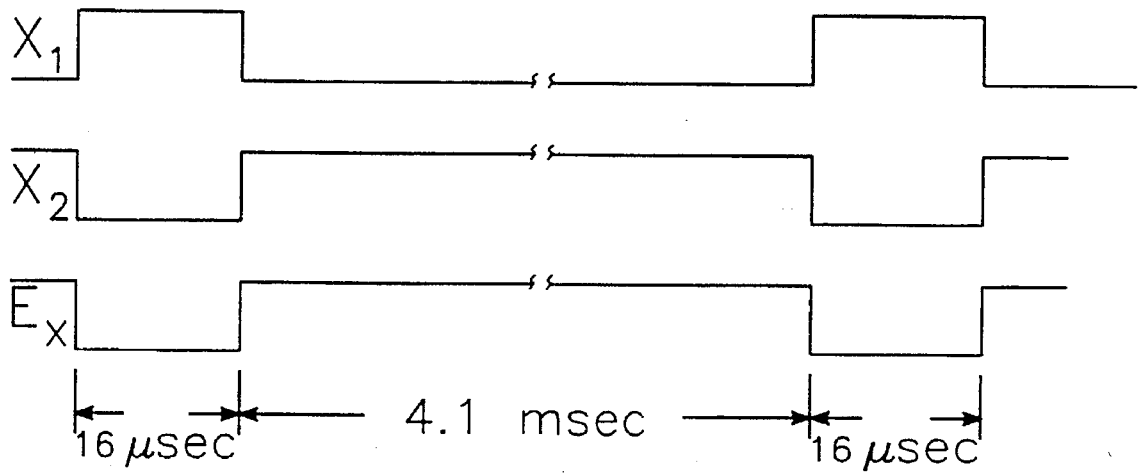
FAST OPERATION
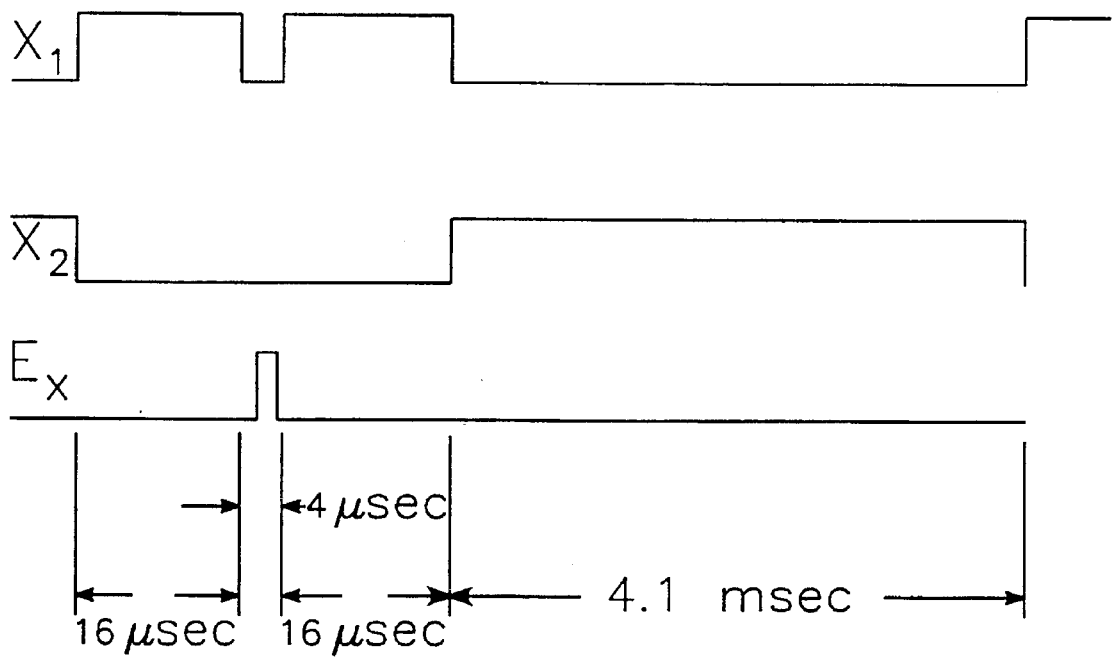
Fig. 8.

SYSTEM FOR ACQUIRING AN IMAGE OF A MULTI-PHASE FLUID BY MEASURING BACKSCATTERED LIGHT

FIELD OF THE INVENTION

The present invention relates to a method and apparatus for analyzing a multi-phase fluid medium, and more particularly, an improved method and apparatus for determining the shape, size and concentration of one or more of the phase components.

BACKGROUND OF THE INVENTION

There are many applications in the material processing industry where it is necessary to monitor and control the composition of a multi-phase fluid medium to obtain certain desired end product qualities. Typical examples are the emulsification and crystallization processes, both of which involve liquid fluid suspensions. Other examples include fluidized beds and dry grinding circuits which involve air suspensions.

In an emulsification process two immiscible liquids are forcefully mixed to produce a distribution of individual droplets of the one liquid suspended within the other. The size distribution of these droplets directly determines the stability of the emulsion. By measuring this distribution one can control the mixing process and the resulting stability of the emulsion.

A crystallization process is used to separate one material dissolved within another. For example, in the batch crystallization of sugar, impure sugar solids are dissolved in a heated, aqueous solution. When this mixture reaches a supersaturated state, the temperature is lowered, which causes the individual sugar molecules to crystallize out of solution by depositing layer-by-layer in a defined pattern along the crystal lattices of the crystalline seed particles. The seed particles are either formed by spontaneous nucleation or are introduced into the crystallizer at the beginning of the process.

The material inside the crystallizer is in multi-phase form. In the case of sugar crystallization, inside a crystallizer apparatus, the solution is typically in a vapor phase (water vapor intermixed with air), a liquid phase (water and the dissolved sugar/molasses mixture), and a solid phase (the sugar crystals). The efficiency and efficacy of the crystallization process critically depends on the extent of the supersaturation, the size and numbers of the seed particles and the dynamics of the mixing action, i.e. the balance between the growth rate and attrition (grinding) effects.

There are typically three physical zones inside a crystallizer, (i) the stable (unsaturated) zone where crystallization is not possible, (ii) the metastable (supersaturated) zone where spontaneous crystallization is improbable, and (iii) the unstable or labile (supersaturated) zone, where spontaneous crystallization is probable. Inside zone (ii) and zone (iii), the material molecules can begin to exhibit molecular alignment within certain clusters (or 'swarms') prior to the occurrence of nucleation and the formation of crystalline solids.

As described in Kerker, *The Scattering of Light*, Academic Press, New York, 1969, density and concentration fluctuations in the solution cause index of refraction changes in the solution, which in turn causes scattering of light. While it is generally very difficult to observe these fluctuations, they do become detectable by measuring properties such as double refraction and the production of interference patterns of polarized light caused by light scattering at the boundaries of these swarms. The detection and measurement of these swarms are an important indicator of the state of supersaturation of the liquid and can predict the onset of spontaneous nucleation.

U.S. Pat. No. 4,871,251 to Preikschat et al. entitled Apparatus and Method for Particle Analysis, commonly assigned to the assignee of the present invention and incorporated by reference, describes an in-line particle analysis system with a measuring window placed into a flow stream. While this type of apparatus does show relative changes in the particle size distribution, it is not able to provide accurate quantitative data on particle size and shape, or the liquid 'swarms' that may be present prior to nucleation. The apparatus described therein evolved into another apparatus the subject of U.S. Pat. No. 5,124,265.

The material characteristics of a multi-phase solution (also referred to as a slurry) can vary widely inside a reactor vessel. For example, inside a continuously operated sugar crystallizer, large heat exchanger plates are mounted to heat (or cool) the super-saturated sugar solution. In addition, large agitator plates move the smaller seed crystals into the 'meta-stable' crystallization growth zone and the larger adult crystals into a separation zone by sedimentation. The final crystal size distribution as measured by a probe depends on a number of factors such as the distance between the probe and the agitator blades, the position of the probe window relative to the flow and the overall probe location. These dynamic variables can all influence the probe readings and must be taken into consideration to properly interpret the measured results.

The above described applications involve liquid suspensions. In many industrial processes air suspensions are frequently used to move, dry or agglomerate a flow of particles. Typical examples are pneumatic conveying systems, fluidized bed suspensions and spray dryers. The former two are used to convey a flow of dry particles. The latter is used to dry and agglomerate fine particles. In all of these cases it may again be desirable to measure or control the size of the particle stream. In the case of pneumatic conveying systems the particle flow velocity may be as high as 100 feet per second. This requires that optical measuring systems have high response speeds in order to monitor the size and shape of individual particles.

In the case of liquid suspensions, the hydrodynamic flow conditions can vary greatly, depending on material characteristics (viscosity, size, and distribution) and the boundary conditions, e.g. distance from the walls of a process vessel. At the walls of a process vessel, there are "dead zone layers" which mask the "real" process conditions inside the vessel. There is also typically a thin turbulent boundary layer at the walls of pipelines used for liquid slurry transport. In the case of pulp flow at 2–5% consistency, this turbulent layer can be as thick as 1 mm. The turbulent "rolling" action of this layer prevents the larger particles from hitting against the walls of the pipeline. The velocity profile, taken radially across a pipe line, is highly peaked with maximum values near the center of the pipe and small values at the walls. The profile is also influenced by the material parameters, the flow speed and the Reynold's number. If the viewing window is placed in line with and parallel to the outer walls, the particle size distribution measured at the walls will differ considerably from that directly inside the flow. The difference becomes larger with increasing slurry concentrations, and becomes significant at concentrations of 20–30%, as typically encountered inside industrial processes.

In the apparatus described in U.S. Pat. No. 4,871,251, particle size distribution is measured by a series of linear, one-dimensional scans of random particle chord lengths. This is convened into a number (or frequency) distribution of these (random chord) lengths, and provides a good relative indication of particle size in the lower size ranges. The measurement does not provide shape information or absolute size measurement in the larger crystal size ranges.

The measurement of crystal shapes can be important, because it is a predictor of material properties. Diamond and coal, for example, are both made of carbon but have an entirely different crystal structure and material properties. By monitoring the shape of newly grown crystals, control of process conditions can be facilitated, resulting in higher product quality.

Microscope imaging techniques are presently the only known method to measure both particle shape and absolute particle size. There are a number of on-line vision analyzer systems, for example:

1. the continuous, on-line analyzer marketed by Flow Vision, Inc under the trademark PED-1 and PED-11, used as an inspection system for plastic melts; and
2. the system marketed by J. M. Canty Associates, Inc. described in U.S. Pat. No. 4,965,601, used as a wall-mounted inspection system.

These systems are used with the viewing window mounted flush with the walls of the reaction vessel (or pipe line) and mainly to measure impurity levels in relatively dilute fluids, like a plastic melt in the plastics extrusion industry. Under these conditions, imaging systems can readily discriminate between individual particles and a high contrast background (either dark in the case of back-scattering, or light in the case of a transmission geometry). They do not readily lend themselves to be used in a probe configuration.

The amount of light back-scattered from a fluent medium depends on the particle concentration, the particle size distribution, the index of refraction of the various phase constituents in the multi-phase medium, the shape of the particles, the turbidity and the absorption coefficient of the medium. At high process concentrations, the material densities are so large that there is little space between the adjacent particles. Because it requires a million small particles (of 1 μm in diameter) to make up the same weight as a single large (100 μm) particle, slurries at high process concentrations contain many more fine particles by number than large particles. When an unfocused, white light source is used as a source of illumination, the light will be multiple scattered from the many individual small particles and will become highly diffused. This makes it difficult to resolve individual particles and has always limited the utility of imaging systems for in-line process applications at high slurry concentrations.

If the material concentration within the fluid medium is sufficiently high, the light beam will be multiple scattered by more than one particle in the beam. This transition from single to multiple scattering is gradual and occurs over a region where about 26% of the light in a collimated beam is obscured by particles in the light beam (see Jones, A. R., *Scattering of Electromagnetic Radiation in Particulate Laden Fluids*, Prog. Energy Combust. Sci., 5, 73–96). In many industrial applications the material concentrations can be so high that over 50% of the light gets obscured in a distance of only a few microns into a slurry flow. Multiple scattered light becomes randomized and depolarized. Further, using a white light source will wash out any features in the scattered light and make it very difficult to see any shadows or contrast between neighboring particles.

Sensor probes intended for in-line use in the chemical processing industry have to meet a number of other requirements, most of which have not been previously addressed until the present invention, a. the viewing window must be capable of being placed directly into a process flow to measure the dynamic changes taking place inside the process;
b. the system must provide fast signal counting and processing rates to measure process information in real time;
c. it must withstand operation at high pressures and over a wide range of process temperatures from cryogenic (−50° C.) to high temperatures (+150° C.) ;
d. include the ability to withstand highly toxic and corrosive materials, survive at high vibration levels and wide range of environmental conditions, and be designed for operation in hazardous environments;
e. include means to extract the probe from the process, while the process is in operation, to remove and clean the probe window;
f. must be able to operate at very high slurry concentrations, as typically encountered at full in-line process concentrations; and
g. it must be able to measure particles over a wide size range from 1 μm to 3000 μm (3 mm).

The above criteria are necessary conditions for a measuring system to be useful in the chemical processing industry, and it is the objective of this invention to provide this capability.

SUMMARY OF THE INVENTION

The present invention describes an optical technique for analyzing undiluted, multi-phase fluid flows as typically encountered inside reactor vessels or flow lines in the chemical industries. In particular the technique uses a pulsed, coherent light source and measures the back-scattered light collected over a wide scattering angle; it utilizes imaging technology with relay optics, and a long probe tube configuration, which can be inserted through a ball valve assembly, or other type of insertion assembly, to measure directly inside a process flow. The backscattered light is then focused on a charge coupled device (CCD) chip.

In one preferred embodiment, a light beam is relayed via a set of lenses down a long probe tube, through a window at a probe tip to illuminate the material that is passing past the window. The light beam is pulsed to "freeze" the motion of the particles streaming past the window. The backscattered light is collected by the same set of optics and is focused on the front surface of a CCD chip. The lens closest to the front window has a short focal length with a large numerical aperture to collect the back-scattered light over a wide range of backward angles, thereby increasing the detection sensitivity to larger particles, which lie behind and are partially obscured by the myriad of smaller particles closest to the window. The probe tube is inserted through an insertion assembly so that the front viewing window is in direct contact with the material flow, and can be positioned so that the flow will provide a continuous and representative stream of material past the window. Best measuring conditions are obtained by placing the probe window at a modest angle of 30°–45° into the flow so that the momentum carried by the particles will force them through the boundary layer at the probe window and cause them to hit against the front window, providing a representative measurement of the physical parameters of the slurry flow. The preferred embodiment combines imaging technology with a specific probe configuration, which is optimized for use in the chemical process industries.

In another preferred embodiment, pulsed light is sent down a fiber-optics cable to provide a side-illumination of the material in front of the viewing window. The back-scattered light again is collected by a set of relay optics.

In both embodiments, the optical light source preferably comprises a pulsed laser diode, as a source of intense, monochromatic and polarized light. The back-scattered light intensity, depends on the scattering characteristics of the material particles (or droplets) carried within the slurry.

In other embodiments, a polarization filter mounted in front of the CCD allows the user to preferentially look at the polarized, or the depolarized light components of the back-scattered light, thereby enhancing the contrast between the backscattered light pulses and the background radiation.

In other embodiments, particularly high speed measuring applications, a high speed light strobing system is described, which is used in conjunction with special timing circuitry to minimize the integration time of the CCD. A specific data handling system is also disclosed which utilizes parallel multi-channel processing to obtain high speed signal handling and display rates.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 3A–3D are polar scattering diagrams for iron particles illuminated by a collimated light source for various particle sizes;

FIGS. 4A–4B are cross-sectional views of a mounting and insertion apparatus formed in accordance with the present invention for a probe;

FIG. 6 is a view of the probe tip configuration formed in accordance with the present invention with three different front lighting configurations;

FIG. 8 is a timing diagram suitable to produce a very short light exposure sequence.

DETAILED DESCRIPTION OF THE PREFERRED EMBODIMENT

Prior to describing in detail the method and apparatus of the present invention, it is helpful to define some terms that are used herein:

The term "light beam" or "collimated light beam" shall mean a pencil of light with a plane wave front radiated from a distant (point) light source, as present in the "far field radiation region".

The term "radiated light wave" or "scattered light wave" is a light wave that is reradiated from a secondary light source. The light wave is in the "near field radiation region", where light intensity diminishes inversely to distance.

The term "backscattered light" refers to that portion of the incident light beam being scattered into backward angles and accepted by the photodetection circuitry.

The "Lambert-Beer law" (or simply "Beer's law") relates to the attenuation of a light beam as it travels through a scattering/absorbing medium, and describes the light intensity I(x) as a function of $I_o$ (the intensity of the light beam at the boundary of the medium, where x=0) and x, the distance into the medium:

$$I(x)=I_o e^{-\mu x},$$

where µ=crAS and r=concentration of the slurry (in % of solids material of total weight)

A=the total optical cross sectional area per unit of solids concentration, and

S=a scattering coefficient c=is a constant.

The term "multiple light scattering" refers to the light scattering process where the light scattered from one particle is rescattered by another neighboring particle. When the particle concentration is sufficiently low, the particles are far enough apart, and the probability for rescattering is small, in which case the "single scattering process" will dominate.

The term "Fraunhofer diffraction effects" or "laser diffraction effects" refers to the specialized case of light scattering, where the scattering particles are illuminated by a collimated light beam and the scattering particles are of a size larger than the wavelength of the light beam.

The term "polar scattering diagram" or "angular dependent diffraction pattern" describes the angular dependence of the light intensity scattered via the "Fraunhofer diffraction effect" and further described in "Particle Size Measurement for the Control of Industrial Crystallizers", Ph.D. thesis of Arthur Boxman, Delft University Press, 1992, Delft, Holland.

The term "anisotropic liquid" refers to certain types of liquids at temperatures just above the melting point where the molecules are aligned into anisotropic regions (see: J. W. Mullin, Crystallization, London, Butterworths, 1961).

Figure 1C:
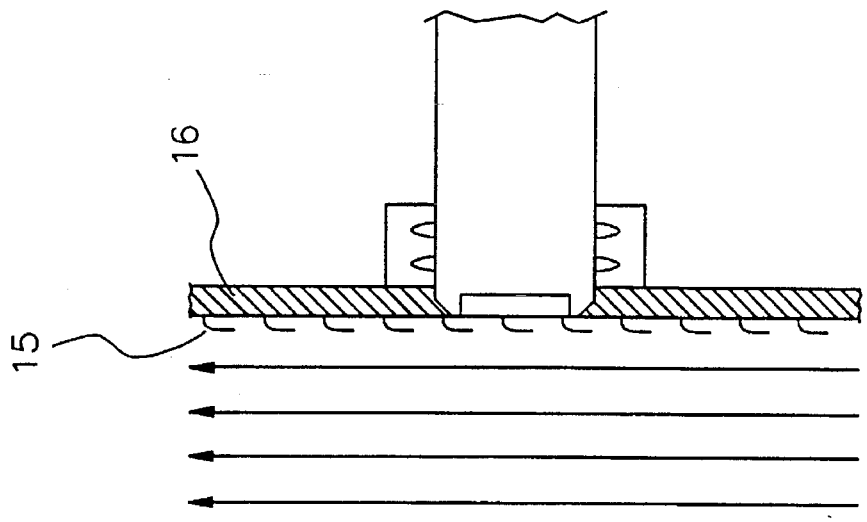
FIGS. 1A–1C illustrate different flow patterns at the tip of a probe placed into a slurry flow.
Figure 1B:
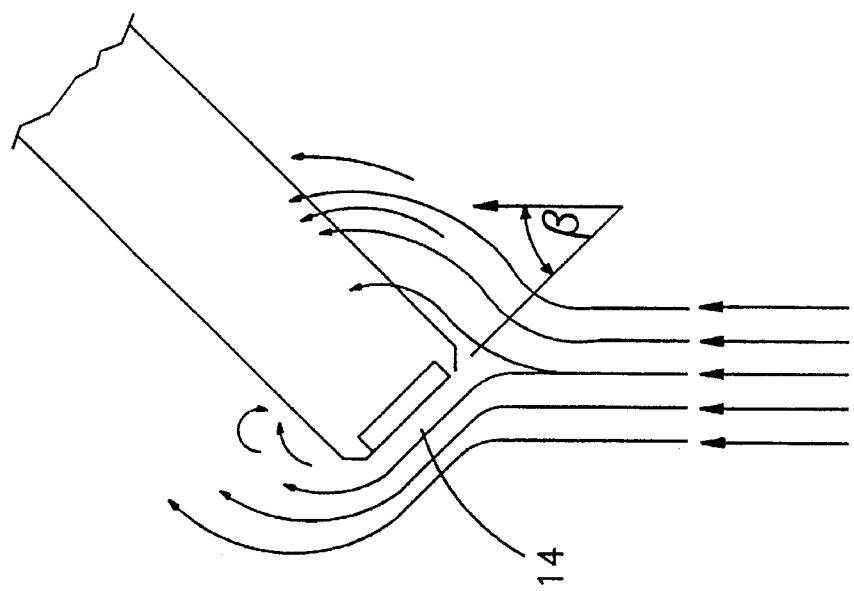
Figure 1A:
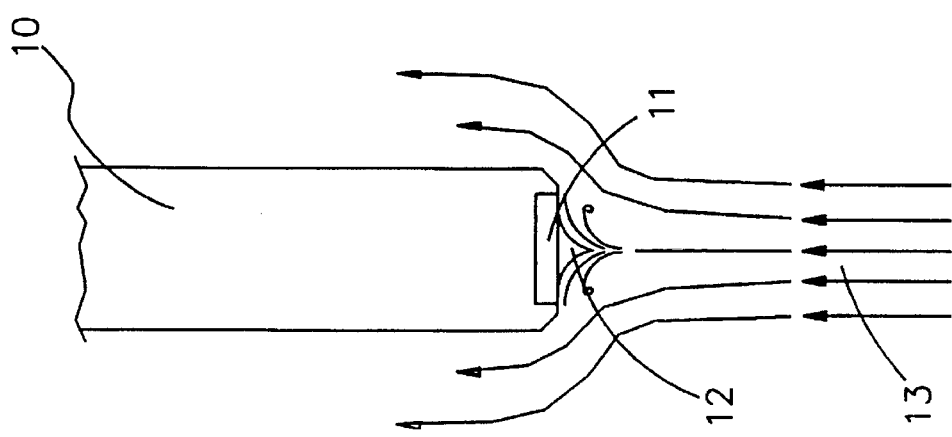

Turning next to a detailed description of the preferred embodiment, FIGS. 1A–1C show a probe tip 10 with a window 11 placed into a moving slurry flow 13. In FIG. 1A, the front surface of the window 11 is normal to direction of the slurry flow 13. In FIG. 1B, the front surface of the window 11 is at angle β to the direction of the slurry flow 13. Finally, in FIG. 1C, the front surface of the window 11 is parallel to the direction of the slurry flow 13. In FIG. 1C, an interior wall 16 of a pipeline carrying the slurry flow 13 is also shown.

Turning to FIGS. 1A, where the window 11 is normal to the slurry flow 13, there is a dead zone 12 in front of the window 11, which causes material from slurry flow 13 to build-up at the front surface of window 11. In FIG. 1C, where the window 11 is parallel to the slurry flow 13, there is a higher amount of flow friction at the wall 16 of a pipeline than at a position away from the wall 16 and interior to the pipeline. The high friction region at wall 16 causes the formation of a turbulent stagnant layer adjacent to window 11 which prevents larger particles from getting close to window 11.

In FIG. 1B, where the slurry flow 13 is at an angle to window 11, there is a smooth and continuous flow past window 11. This is because the larger particles have enough momentum to cause them to continue to flow in a straight line and penetrate the layers near the window 11 and to scrape past the window 11. This scraping action prevents the build-up of a dead zone 12 as in FIG. 1A and also aids in keeping the window free from material. In the preferred embodiment, angle β is between 30° and 45°.

Figure 2:
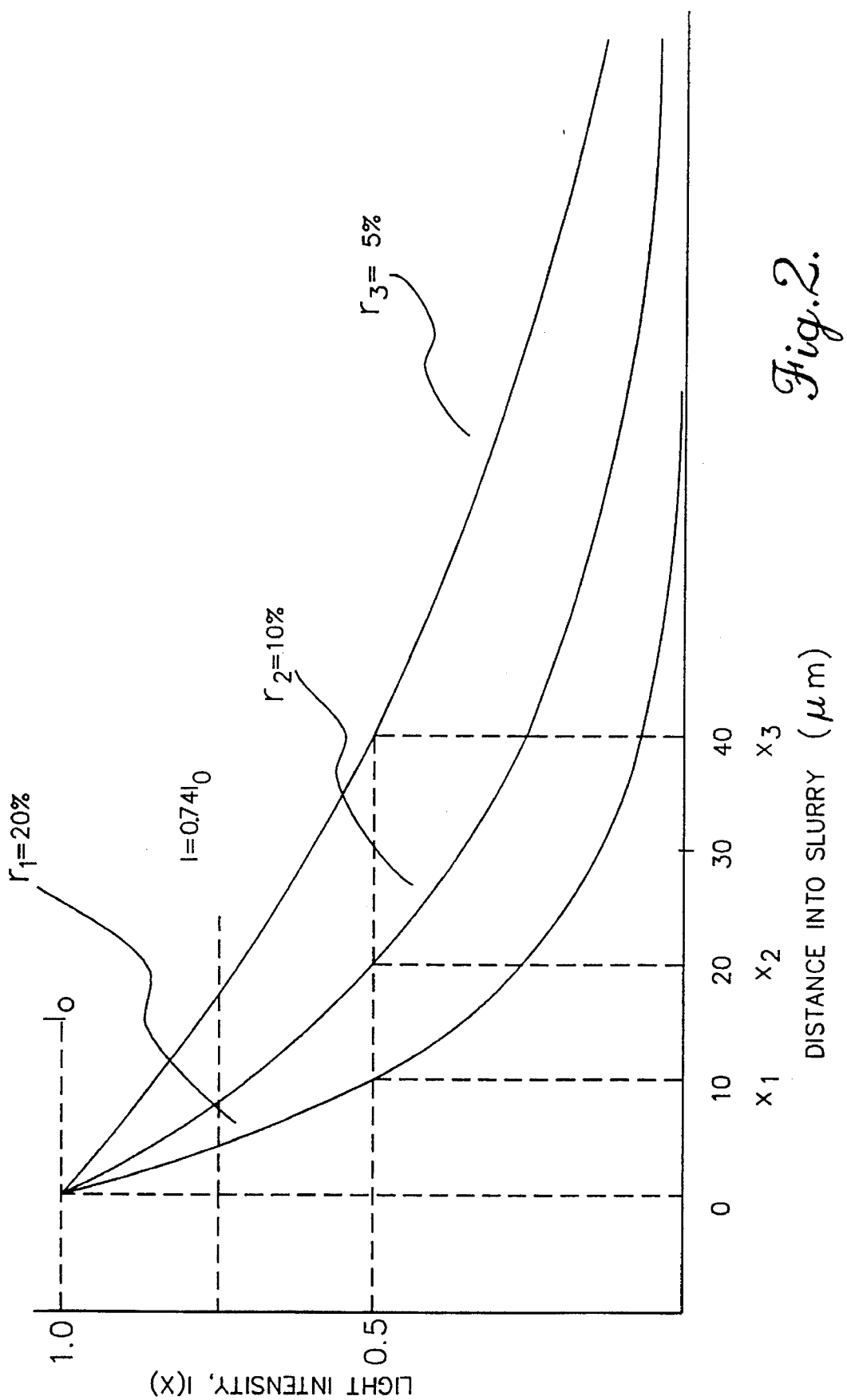
FIG. 2 shows the attenuation of a light beam passing through a slurry flow.

FIG. 2 illustrates the attenuation of a light beam as it propagates through window 11 into the slurry flow 13. As will be seen in greater detail, in operation the present invention passes a beam of light through window 11 into slurry flow 13 to capture an image of the flow. In accordance with Lambert-Beer's law, the intensity of the light beam decreases exponentially with increasing distance x into the slurry flow 13. Assuming x=0 at the front (inner) surface of window 11 that is in contact with the slurry, the intensity I(x) drops by half at distances of $x_1$, $x_2$ and $x_3$ for slurry densities $r_1$, $r_2$ and $r_3$ respectively. The "half distances" are 10, 20 and 40 μm for the corresponding densities of 20, 10 and 5% (by volume). According to Van de Hulst (*Multiple Light Scattering, Tables, Formulas and Applications*, Volumes 1 and 2, Academic Press, New York, 1980) multiple light scattering occurs at a light obscuration of about 26%. In a transmission mode, neglecting light absorption effects, this corresponds to a value of I(x)=0.74. If the light intensity drops below that value, one can assume that the back-scattered light has undergone multiple scattering.

In a typical example of ground calcium carbonate with a mean size of 20 μm and a density $r_1$ (by volume) of 20%, the "half distance" $x_1$ is about 10 μm. Thus, the intensity of the illuminating light beam drops to about half its initial value after traversing a distance of 10 μm into the slurry. At a slurry density of 5%, the half distance would be 4 times as large, or 40 μm. The large attenuation of light intensity in a slurry flow is the result of multiple light scattering. At higher material concentrations the light waves radiated from individual particles get completely washed out and are very difficult to detect using an optical imaging system.

FIGS. 3A–3D show four polar diagrams of the angular dependent light intensity for four different scattering processes. The FIGURES illustrate the effect of a light beam 20 incident on an opaque iron particle 21. The particle will preferentially scatter light into the forward direction, with some of the light being diffracted into all other angles. The polar angle α denotes the scattering angle from the forward direction of α=0 and the circles denote the relative amplitude of the scattering intensity. Each circle denotes an order of magnitude increase in the intensity from relative intensity $10^0$ to $10^7$ in magnitude. The four scattering diagrams, FIGS. 3A–3D, show the angular dependent intensity for four different iron particles 21, each of a different size. In these diagrams, the particle sizes have a diameter D of 0.7, 1.4, 3.5 and 14 μm respectively. In each case the intensity function is highly peaked into the forward direction with a superimposed characteristic diffraction pattern. At backward scattering angles, the absolute value of the light intensity increases with the cross-sectional area (proportional to $D^2$) of the particle.

It should be noted that the attenuation factor (μ in Lambert Beer's law) depends very much on the total cross sectional surface area of the particles suspended in the slurry. In the case of three different slurry suspensions, all made of the same material at the same concentration, each containing a different mono-sized particle size distribution made up of particles with diameter of 1 μm (fine), 10 μm (medium), and 100 μm (large) size respectively, the surface area of the distribution of fine particles (of 1 μm in size) is 100 times larger than that of large particles (100 μm ), even though both have the same concentration by weight.

The light source used in the present invention to generate an irradiating light beam is a laser diode. As is known in the art, the light output from a laser diode has a Gaussian shaped intensity function along the z-direction, normal to the direction of beam propagation with z=0 at the center of the beam, as follows:

$$\exp(-2z^2/s^2)$$

where s is the full beam width at half of maximum beam intensity $I_o$. When a light beam from a laser diode propagates through the front surface of a window located at x=0 through a slurry flow, the light will be attenuated. The amount of attenuation is dependent upon the size of the particles in the slurry flow. For example, it has been shown that slurry flows having particles on the order of 1 μm exhibit significantly higher light attenuation per unit of slurry concentration than slurry flows having particles in the 10 μm range. Similarly, slurry flows having particles on the order of 10 μm exhibit significantly higher attenuation in light beam intensity than slurry flows having particles in the 100 μm range. In other words, a light beam is able to penetrate orders of magnitude further into a slurry with the large size particles, as compared to the small size particle distribution at the same slurry concentration. In a normal industrial application, of course, one does not typically encounter mono-sized distributions. Nonetheless, experimental data clearly illustrates that the presence of a small amount of fine particles can greatly limit the penetration depth of a light beam into a concentrated slurry flow.

To overcome the flow conditions shown in FIGS. 1A and 1C, it is necessary to insert the probe tip 10 directly into the slurry flow 13 away from the wall 16 of the pipeline. FIGS. 4A and 4B show a mounting apparatus that allows probe tip 10 to be inserted into a pipeline while the process is in operation. The probe tip 10 of probe body 28 is inserted through a ball valve 31 and mounting assemblies 26 and 25 such that window 11 is in direct contact with slurry flow 13. The tubular mounting assembly 25 is welded at an angle β to the wall 16 of a pipeline or process vessel, with a probe shield 30 going through wall 16 and protecting the side of the probe 10. The ball valve 31 allows the probe 10 to be inserted into (or extracted from) a continuously operating process. A locking collar 33 is attached to probe body 28 and is used to lock the probe body to a flange 32. An O-ring assembly 39 provides a pressure seal, and all parts are built to withstand high process pressures.

The probe is extracted by unlocking the locking collar 33, sliding the probe body 28 and locking collar 33 along two guide bars 37, past a safety bar 35 until locking collar 33 abuts against a toggle bolt assembly 36. The ball valve 31 can then be closed by rotating handle 38 through 90°. The toggle bolt 36 is removed to allow the probe to be fully extracted. The probe is reinstalled following the above procedure in reverse. With the ball valve 31 closed, the end tip of safety bar 35 determines the maximum insertion distance of locking collar 33 to prevent the window 11 from being impacted against the closed ball of the valve assembly. When the ball valve handle 38 is opened, safety bar 35 is removed allowing locking collar 33 to be moved back into its lockable position. The probe body and all parts of the ball valve assembly in contact with the slurry flow 13 are made of titanium to withstand the corrosive environment typically encountered in the chemical process industry.

In some crystallization applications, the volume between the probe tube 10 and the probe shield 30 may accumulate crystallized material. In this case, it may be difficult to remove the probe assembly without first dissolving the crystallized material using a flow of heated suspension liquid. This can be done on a continuous basis by injecting a pressurized flow of suspension liquid into the probe shield through the pipe fitting 34 at the side of the ball valve assembly. In a crystallization process, heating the injected suspension liquid to a temperature at least 10° C. above that of the probe will eliminate crystallized solids build-up at the probe. The above describes the preferred embodiment for mounting the apparatus of the present invention into a slurry flow in an in-line process. It can be appreciated by those skilled in the art that other mounting techniques and apparatus may be utilized to place the probe tip 10 into a slurry flow. The crucial aspect of the disclosed mounting apparatus shown in FIGS. 4A and 4B is that the window 11 of the probe tip 10 be inserted into the slurry flow.

Moreover, in order to adapt imaging technology for use with the above described type of probe configuration at high process concentrations, pressures and temperatures, several particular requirements should be met: (1) the light source and detector assemblies should be located at a remote location, away from the high temperatures of the process environment; (2) the illuminating beam should have a thin, pencil-like beam shape to provide maximum penetration into a concentrated slurry flow; (3) the back-scattered light should be collected over as wide an angle as possible to (i) optimize the collection efficiency and (ii) to average out the angular dependent diffraction effects; (4) the image at the window should be magnified by an order of magnitude to distinguish particle sizes down to about 1 µm near the wavelength of the illuminating light source; (5) monochromatic light should be used to minimize chromatic aberration effects in the optical system; and (6) pulsed (or strobed) light bursts should be used to "freeze" the action of the particle flow moving past the window.

Figure 5:
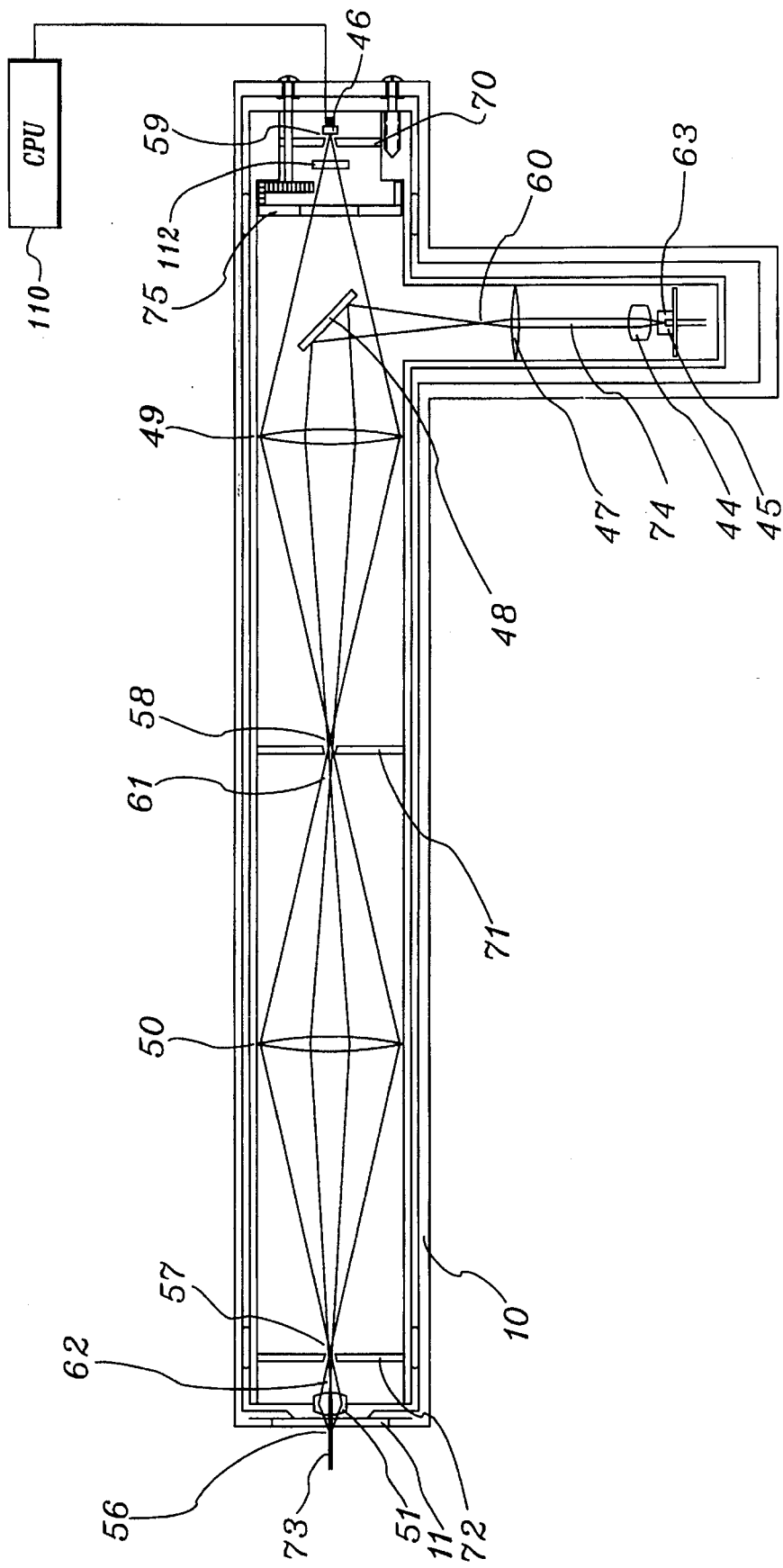
FIG. 5 is a light transmission system formed in accordance with the present invention to relay the collimated light from the light source to the probe window and the back-scattered light to a CCD detector system.

These requirements are realized by using an optical configuration as shown in FIG. 5. As seen, a laser diode 45 and a CCD photodetector 46 both utilize the same relay optics comprising a beam splitter 48, lenses 49, 50 and 51 and window 11. The light emitted from the laser diode 45 is in an elliptical shaped pattern and is shaped by lens 44 into a collimated beam 74. Collimated beam 74 is then focused by lenses 47, 49 and 50 to focal points 60, 61 and 62 respectively. Beam splitter 48 redirects the light from diode 45 onto lens 49. The beam splitter 48 allows the outgoing light from diode 45 and the backscattered light to follow along the same path through lenses 49, 50, and 51. After the outgoing light is transfered from lens 49 to lens 50, lens 50 transfers the light onto lens 51. Lens 51 then again collimates the light to produce a very thin, intense illuminating beam 73, which is emitted by lens 51 through window 11 to illuminate the slurry flow going past the window. In the preferred embodiment, the width of beam 73 is as wide as the largest particle to be measured, typically 1–3 mm in diameter.

In the optical system, comprising lenses 50 and 49, the object distance $L_o$ is equal to the image distance $L_i$; this means that the distances between focal point 57 and the center of lens 50, between points 50 and 58, between points 58 and 49 and between points 49 and 59 are equidistant. The object distance $L_o$ and image distance $L_i$ are related to the focal distance F of the relay lenses 50 and 49 as: $1/F = 1/L_o + 1/L_i$. If $L_o = L_i$, then $L_o = L_i = 2F$. If there is a large temperature rise at the probe the length of the probe will expand. This causes an increase in the object distance and, given by the lens formula, a corresponding decrease in the image distance. In the optical system as herein described, the effect of a thermal expansion is thus self-compensating. If needed, the light signal can be further relayed by adding additional relay lenses with the same focal length as lenses 50 and 49.

High speed image sensor arrays are commercially available. For example, the DALSA (type IA-D1) CCD image sensor can process up to 220 frames/second of 256×256 array elements resolution, each array element (or "pixel") measuring 16 µm by 16 µm in size. There is a direct one-to-one correlation between the "object size" at focal point 56 and the "image size" at the CCD. The magnification factor M is determined by lens 51 and is the ratio of the distance from focal point 57 to the center of lens 51 to the distance between focal point 56 and center of lens 51. FIG. 5 shows the special case of a magnification factor M of 2, which puts the minimum resolving power of the referenced CCD imager at about 7 µm. At a M of 16, the resolving power would be as small as 1 µm, ignoring limitations imposed by diffraction and various chromatic aberration effects.

FIG. 6A shows a close-up view of the light beam configuration at the front of the window, in this case with a magnification factor of M=4. The illuminating light beam is focused at point 62, which is also the focal point of lens 51. The lens collimates the beam which then shines through the front of the window 11 and penetrates into the slurry flow. The same lens 51 is used to collect the back-scattered light beam; it has a large numerical aperture to collect the light over as wide a range of angles 53 as possible and focuses that light at focal point 57. This light is relayed back through lenses 50, 49 and is focused at focal points 58 and 59 respectively, the latter being on the front surface of CCD detector 46. Beam stops 72, 71 and 70 are positioned near the respective focal points and prevent most of the secondary light, outside of collection angle 53, from reaching the detector.

FIGS. 6B and 6C show two alternative ways of illuminating the region of interest. In the configuration shown in FIG. 6B, the laser light goes through a fiber-optics cable 84 and is focused by a GRIN lens 83 at focal point 62 with lens 51 again producing a collimated light beam in front of the window. The light is reflected by the fully reflecting prism 82 and the beam splitter 80. In the configuration shown in FIG. 6C, the light from fiber-optics cable 87 is collimated by GRIN lens 86 and again is centered in the centerline of lens 51 to uniformly illuminate the region seen by the CCD. The width 73 of the collimated beam is slightly larger than the width of the CCD divided by the magnification factor M. For example, when using a CCD with a 256×256 pixel array, the size of the CCD aperture is 4.096×4.096 mm, and the diagonal is 5.793 mm. In this case, the width of the collimated beam should be at least 6 mm divided by M, or 1.5 mm for M=4.

In accordance with Beer's law, the particle detection efficiency also depends on how far the focal point 56 is moved inside the slurry flow. If the focal point 56 is near the window, the system will predominantly be sensitive to the smaller particles near the window. If the focal point is moved further into the slurry, the smaller particles will be washed out and the larger particles, with a higher scattering light intensity proportional to the $D^2$ (D=particle diameter), will become more visible. The particular configuration in FIG. 6C, shows the window positioned at an angle "gamma" to the plane containing focal point 56 and lens 51, to provide a variable distance between focal point 56 and the window 11. All of the optical parts are mounted to probe tube 10.

It should also be noted that particles of different size will show a different degree of depolarization. This effect can be utilized to obtain a better signal-to-noise ratio to discriminate between small and larger particles. The light output from a laser diode is already linearly polarized. If laser diode 45 is mounted so that the linear polarization vector is normal to the scattering plane (the plane which holds points 63, 61 and 64) a polarizing filter 75 can be used to select the polarized or unpolarized components of the backscattered light.

To analyze individual particles in a moving slurry flow, it is necessary to pulse or strobe the light source fast enough to freeze the smallest particles in flight. The maximum pulse duration $T_{max}$ for the light pulse is determined by the smallest particle size detection threshold $S_{min}$ and the maximum flow velocity $V_{max}$, as follows:

$$T_{max} = S_{min}/V_{max}$$

If $S_{min}$ is 1 µm and $V_{max}$ is 0.5 m/sec, then, for a pulse duration of 1 microsecond, the particle will have moved a distance of 0.5 µm, and will still be detected by the same single pixel of the CCD. If the flow speeds are much higher, e.g. 50 m/see, it is necessary to use a pulse duration as short as 10 nanoseconds to achieve the same pulse resolution. Moreover, to measure the backscattered light during a single pulse exposure, it is necessary that each light pulse have sufficient light intensity.

Various pulsed light sources are commercially available. Xenon flashlamp systems produce light pulses over a wide spectral range (from 200–1000 nm) with pulse widths (full width at half max) in the 2–10 µsec range. Xenon flashlamps do not make ideal light sources because pulse durations are too long, the spectral range is too broad and the light source is too diffuse and low in power output level. Nanosecond flashlamp systems are available, e.g. type IBH from Oriel, which have pulse widths as short as 1 nsec, but with very low light intensities of $10^{10}$ photons/pulse (equivalent to about $10^{-9}$ Joule per pulse). High pressure Nitrogen lasers can produce monochromatic light pulses of both short duration (0.6 nsec) as well as high intensity (100 µJoule/pulse) but have a very limited life time of $10^8$ pulses, equivalent to an operational life of 100 days at a continuous pulse rate of 10 pulses per second.

Laser diodes, used in conjunction with a high speed trigger device, provide high light output, short light pulse durations with long operational life times. For example, U.S. Pat. No. 4,818,099 commonly assigned to the assignee of the present invention, incorporated by reference, discloses laser diodes suitable for such use. A laser diode, type SG2010A from EG&G Optoelectronics or type C86083E from GE Canada Inc, Electro Optics Div., can be pulsed using a fast avalanche discharge to achieve very high power output levels for exceedingly small periods of time ranging from a few nanoseconds to 0.2 µsec in time. A SG2010A laser diode, with a peak power intensity of 10 W, driven with a pulse duration of 0.1 µsec, produces a power output level of 1 µJoule per pulse.

In comparison the DALSA (type IA-D1) CCD image sensor is driven into saturation at a light intensity of 0.045 µJoule/cm²/pulse. In a typical application, the output from the laser diode will be adjusted in such a way that the size of the (laser) beam spot at the front window 11 will be comparable in size to the cross sectional area of the CCD. This means that if only 1/20 of the laser output energy is returned, the CCD will be driven to saturation at its full maximum output level.

A standard CCD imaging device is continuously exposed to light, while the array elements are read out on a sequential line-by-line basis. The effective light exposure integration times are of the order of 10 milliseconds for an output rate of about 100 frames per second. Using a laser light flash with a pulse length of 0.1 µsec, each pulse takes up only one part in $10^5$ of the total duty cycle; the rest of the time there would be no light signal and the CCD would only pick up dark current and ambient (non-laser) light. The signal-to-noise ratio of the CCD output is inversely proportional to the light exposure integration time. The shorter the integration time with respect to the pulse length of the light flash, the higher the signal to noise level.

Figure 7:
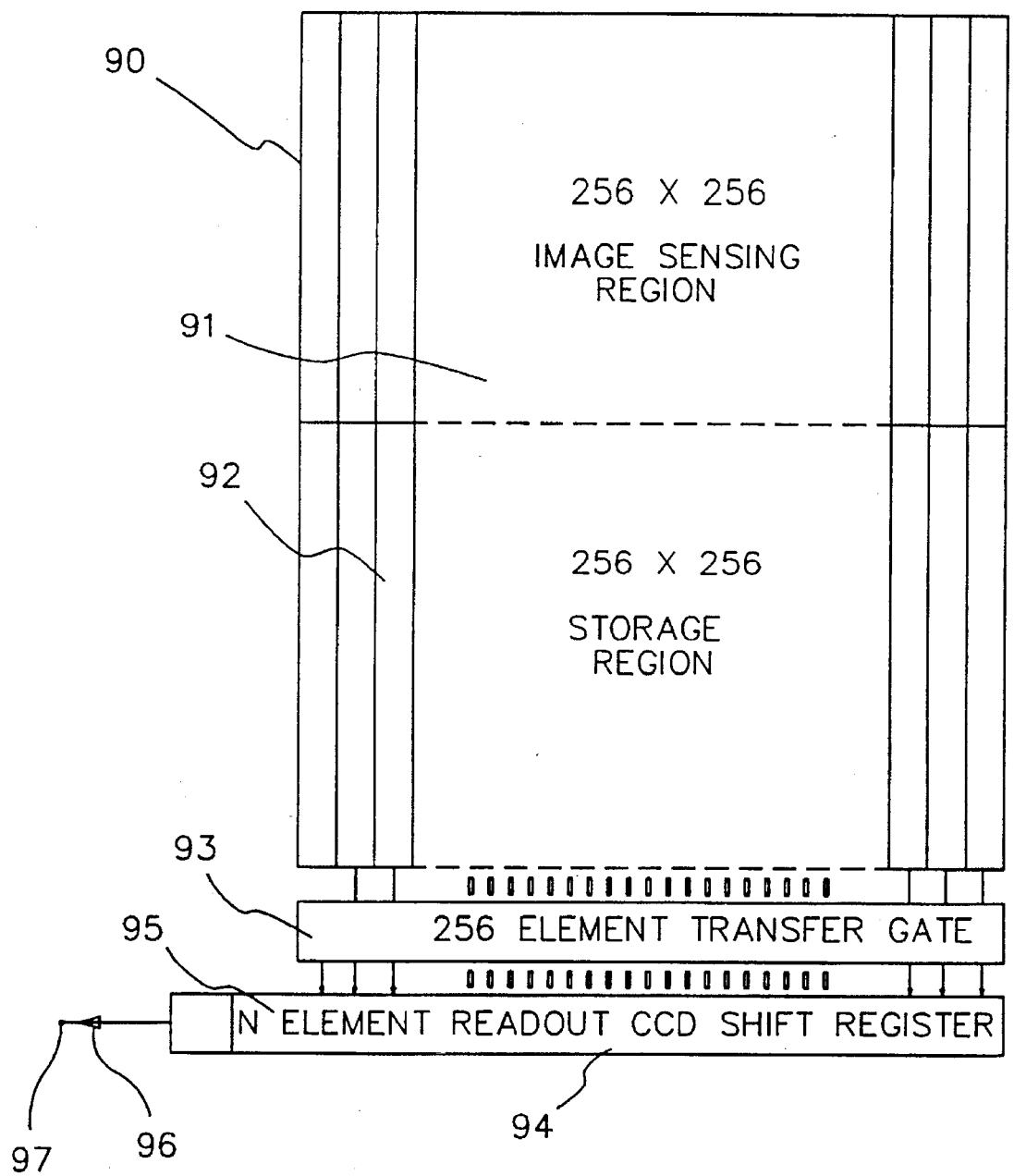
FIG. 7 is a block diagram of a CCD image sensor with built in storage memory array.

This invention also describes the use of a special type of CCD image sensor with a specific timing arrangement to achieve much shorter exposure integration times than are normally achievable. FIG. 7 shows a block diagram of the DALSA CCD image sensor 90 (type IA-D1). This particular image sensor has a special architecture in that it contains both an image sensing region 91 (an area array consisting of a square matrix of 256×256 photo elements) and built-in storage register 92 (an additional square matrix of the same size with 256×256 storage cells). The 256 lines of photoelements in the imaging region are first transferred on a line-by-line basis to the storage region, and then the information is serially transferred out of the storage region via the CCD shift register 94. The data clock rate is 16 MHz, which means it takes 0.06 µsec to shift out one data element, 16 µsec for one line element (of 256 elements), and 4 msec for a whole frame, for a maximum frame rate of 220 frames/sec. Under normal operation the CCD image array is exposed during the entire time it takes to transfer one complete frame, i.e. 4 msec.

During light exposure, signal is collected in the imaging sensing region CCD. At the end of the exposure time, the entire frame, consisting of 256 lines of data, is transferred at high speed into the storage region CCD 92. Each data line consists of 256 elements, all of which are transferred in parallel at the maximum clock rate of 18 MHz. This means it takes 256 clock cycles, or 16 µsec (=0.0625 µsec×256) to transfer the complete array of photoelements to the storage array. During this transfer time (from image region to storage region, referred to below as "X1", the time of first transfer) invalid data is transferred out of the readout CCD. Exposure then starts for the next frame; during this time (of the second transfer, hereinafter "X2") the data from the storage region is transferred line by line to the readout shift register 94 and then, element-by-element, to the output 97. The transfer to the shift register is controlled by a 256 element transfer gate 93. Under normal operating conditions the image sensing region would be exposed for the entire time X2 of data transfer, which, at a clock rate of 16 MHz, would take 4.1 milliseconds (256×256×0.063×10⁻⁶).

FIG. 8 shows the operation of the CCD image sensor in the "normal" mode as well as in the preferred "fast" exposure mode. In the former, transfer cycle X2 follows immediately after transfer cycle X1; exposure time "$E_x$" coincides with cycle X2. In the modified fast mode, there are two successive X1 transfer cycles, each lasting 16 µsec with a short 4 µsec wait period in between. The first X1 pulse is used to clear the image array and the second to transfer the exposed image array to the storage array. In this case the $E_x$ exposure time is very short, e.g. 1 µsec, and occurs during this wait period solely to trigger the light flash. Following the second X1 pulse the X2 transfer cycle is then initiated. Using this timing sequence, the total exposure time is the wait period plus the X1 transfer time, a total of about 20 µsec, as compared to a total exposure time of 4.1 msec. This effectively increases the signal-to-noise ratio by a factor of 200.

In the case of high ambient light conditions, it may not suffice to use the CCD image sensor in the fast mode operation. In that case it may be necessary to use an additional fast light shutter 112 to prevent the ambient light from reaching the CCD during extended integration times. For example, by using an electronically activated Pockels cell, type LX415 from Cleveland Crystals, Inc., one can open an electronic shutter for very short time periods of less than 1 μsec up to 5 μsec to allow most of the transmitted and back-scattered light to pass. When the shutter is closed most of the ambient light is prevented from passing through.

With the detailed description of each of the elements of the present invention as well as their operation described above, it is instructive to describe the operation of the system. In the example provided herein, the probe tip 10 is placed within a moving slurry flow 13. The angle of insertion β is optimized to be between 30° and 45°. As the slurry flow 13 moves past the window 11, video images of the particulate matter in the slurry flow 13 can be periodically obtained. Turning to FIG. 5, the laser diode 45 outputs a pulse of coherent monochromatic light. The light pulse is collimated and relayed via optics 44, 47, 48, 49, 50, and 51 out window 11 as a beam 73. As the beam is incident upon the slurry flow 13, particulates therein backscatter the light beam. The backscattered light is captured by lens 51 and relayed back via optics 51, 50, and 49 and focused on CCD device 46. The CCD device then can generate an image that is substantially similar to a "picture" of the slurry flow 13. As noted above, the magnification of the image provided to CCD 46 is dependent upon the lens 51. In addition, by changing lens 51, the focal point of the "object image" can be changed to be at window 11 or further into the slurry flow 13. It can be appreciated by those skilled in the art that for different applications, lens 51 must be modified. For example, to examine an image further into the slurry flow 13, the focal point of the lens 51 should be increased.

The images focused on CCD are then relayed to a computer processor 110 for further analysis. The provision of images in the manner set forth above is advantageous because a real time visual analysis of a process by a system operator can be made. By providing the ability to a system operator to "eyeball" a process rather than merely have a particle size distribution in numerical format (as in the prior art), it is easier to monitor a process. In addition, because the CCD device provides an array of discrete pixel elements, the shape as well as the size of the particulates can be determined. In some applications, the shape of the particulates suspended in the slurry flow can be important.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for providing an image of a fluid medium, the apparatus comprising:

a probe for insertion into said fluid medium said probe including a window at the tip of said probe, and said probe placed in said fluid medium, such that said window is disposed at an insertion angle to a direction of flow of said fluid medium, said probe further positioned through a ball valve assembly to allow said probe to be extracted without disrupting the flow of said fluid medium, further wherein the ball valve assembly includes a fitting to allow a heated flow of suspension fluid into be injected to said fluid medium;

a light source for generating an illuminating light;

a light transmission system for transmitting said illuminating light from said light source to said window and directing said illuminating light through the window into said fluid medium; and a photodetector for detecting backscattered light from said fluid medium, said photodetector comprising an optical system for collecting said backscattered light over a collection angle to form an optical image of said fluid medium, said optical system using said light transmission system for relaying the optical image to a processor.

2. An apparatus for providing an image of a fluid medium, the apparatus comprising:

a probe for insertion into said fluid medium, said probe including a window at the tip of said probe, and said probe placed in said fluid medium such that said window is disposed at an insertion angle to a direction of flow of said fluid medium;

a light source for generating an illuminating light;

a light transmission system for transmitting said illuminating light from said light source to said window and directing said illuminating light through the window into said fluid medium;

an optical shutter; and a photodetector for detecting backscattered light from said fluid medium, said photodetector comprising an optical system for collecting said backscattered light over a collection angle to form an optical image of said fluid medium, said optical system using said light transmission system for relaying the optical image to a processor, wherein the backscattered light goes through said optical shutter, said optical shutter only open for the duration of the illuminating light.

\* \* \* \* \*